(12) United States Patent
Bouvier et al.

(10) Patent No.: US 7,857,772 B2
(45) Date of Patent: Dec. 28, 2010

(54) STRIDE-MONITORING DEVICE

(75) Inventors: Alain Bouvier, Revel (FR); Roland Blanpain, Entre-Deux-Guiers (FR)

(73) Assignee: Commissariat a l'Energie Atomique, Paris (FR)

(*) Notice: Subject to any disclaimer, the term of this patent is extended or adjusted under 35 U.S.C. 154(b) by 55 days.

(21) Appl. No.: 10/574,287

(22) PCT Filed: Oct. 7, 2004

(86) PCT No.: PCT/FR2004/050493
§ 371 (c)(1),
(2), (4) Date: Mar. 31, 2006

(87) PCT Pub. No.: WO2005/034751
PCT Pub. Date: Apr. 21, 2005

(65) Prior Publication Data
US 2007/0123806 A1    May 31, 2007

(30) Foreign Application Priority Data
Oct. 10, 2003  (FR) ................................. 03 11883

(51) Int. Cl.
*A61B 5/103* (2006.01)
*A61B 5/117* (2006.01)
*A43D 1/00* (2006.01)
*G01C 19/36* (2006.01)
*G01C 19/00* (2006.01)
*G01C 17/18* (2006.01)
*G01C 17/00* (2006.01)
*G01C 17/04* (2006.01)
*G01C 17/30* (2006.01)

(52) U.S. Cl. ............................ 600/595; 33/3 A; 33/3 B; 33/6; 33/316; 33/318; 33/319; 33/321; 33/355 R; 702/160; 482/8

(58) Field of Classification Search ................. 600/595, 600/181, 583, 584; 33/6, 3 A, 3 B, 316, 318, 33/319, 321, 355 R; 702/160; 482/8
See application file for complete search history.

(56) References Cited

U.S. PATENT DOCUMENTS 3,355,942 A * 12/1967 Freeman .................... 73/178 R (Continued)

FOREIGN PATENT DOCUMENTS

| CA | 1 193 436 | 9/1985 |
|---|---|---|
| DE | 297 01 308 | 6/1997 |
| JP | 2003-337930 | * 12/2003 |

OTHER PUBLICATIONS

English Translation of JP 2003-337930.*
U.S. Appl. No. 10/582,764, filed Jun. 13, 2006, David.

*Primary Examiner*—Max Hindenburg
*Assistant Examiner*—Sean P Dougherty
(74) *Attorney, Agent, or Firm*—Oblon, Spivak, McClleland, Maier & Neustadt, L.L.P.

(57) ABSTRACT

A stride monitoring device that can be used particularly for sports applications and that includes a pair of shoes, one of which includes at least one magnetic mass, and the other includes at least a measurement device to make at least one measurement, and a processor for processing of the measurement. The measurement device includes at least one accelerometer and at least one magnetometer capable of outputting signals that can be processed to determine stride parameters.

17 Claims, 4 Drawing Sheets

U.S. PATENT DOCUMENTS

| | | | | |
|---|---|---|---|---|
| 4,571,680 A * | 2/1986 | Wu | .............................. | 377/24.2 |
| 5,485,402 A * | 1/1996 | Smith et al. | ................... | 702/160 |
| 5,807,283 A | 9/1998 | Ng | | |
| 6,122,960 A | 9/2000 | Hutchings et al. | | |
| 6,594,617 B2 * | 7/2003 | Scherzinger | ................. | 702/160 |
| 7,019,647 B2 | 3/2006 | Flament et al. | | |
| 7,188,439 B2 * | 3/2007 | DiBenedetto et al. | .......... | 36/132 |
| 2003/0018430 A1 * | 1/2003 | Ladetto et al. | ............... | 701/217 |
| 2003/0097878 A1 * | 5/2003 | Farringdon et al. | ............ | 73/819 |
| 2004/0173220 A1 * | 9/2004 | Harry et al. | ................... | 128/892 |
| 2005/0125191 A1 | 6/2005 | David et al. | | |
| 2005/0245839 A1 * | 11/2005 | Stivoric et al. | ............... | 600/549 |
| 2007/0111753 A1 * | 5/2007 | Vock et al. | ................ | 455/552.1 |

\* cited by examiner

STRIDE-MONITORING DEVICE

BACKGROUND OF THE INVENTION

Field of the Invention

This invention relates to a stride monitoring device for a walker or a runner.

It can be used particularly in sports and medicine applications.

Discussion of the Background

Devices are known that are installed in pairs of shoes and are designed to monitor some parameters. A device of this type can include a magnetic mass placed in one of the shoes, and a measurement means placed in the other shoe.

The following documents in particular contain further information:

[1] DE 29701308 A
[2] CA 1193436 A.

Document [1] describes an electronic device for measurement of the movement of a foot in a shoe, for example by means of Hall effect transducers and magnets fixed to the sole of this shoe.

Document [2] describes a device designed to warn a child when he puts a shoe on the wrong foot, by means of a magnet placed in one of the shoes and electrical and magnetic means placed in the other shoe.

It should be noted that these documents do not describe the use of an accelerometer or a magnetometer.

SUMMARY OF THE INVENTION

The purpose of this invention is to solve the problem of obtaining information about the stride of a walker or a runner.

It is intended to measure parameters characteristic of the stride and possibly other parameters complementary to the previous parameters (particularly foot movements), using appropriate means contained in the shoes of the person whose stride is being monitored.

The invention proposes to use at least one magnetometer to make measurements of the magnetic field and at least one accelerometer to make acceleration measurements during displacement of the device so as to calculate the position of this device in space.

Specifically, the purpose of this invention is a stride monitoring device, this device comprising a pair of shoes comprising first and second shoes, the first shoe comprising at least a magnetic mass, the second shoe comprising at least measurement means to make at least one physical measurement, and electronic means for processing of this physical measurement, this device being characterised in that the measurement means comprise at least one accelerometer and at least one magnetometer capable of outputting signals that can be processed to determine stride parameters.

It should be noted that the insertion of the components of the device in the pair of shoes makes it possible not to hinder the person who is wearing these shoes and results in a discrete device.

According to one preferred embodiment of the device according to the invention, each of the first and second shoes comprises at least one magnetic mass, measurement means for making at least one physical measurement, and electronic means for processing this physical measurement, the measurement means comprising at least one accelerometer and at least one magnetometer capable of outputting signals that can be processed to determine the stride parameters.

Preferably, the magnetic mass comprises at least one permanent magnet.

The measurement means can comprise a plurality of accelerometers.

Similarly, the measurement means can include a plurality of magnetometers.

Preferably, the electronic processing means are provided with means of transmitting a signal output by these electronic processing means.

According to one particular embodiment of the device according to the invention, this device also comprises portable means designed to receive the signal transmitted by the transmission means and to display data representative of this signal.

Preferably, these portable means comprise:
data reception means,
electronic means for processing these data, these electronic data processing means being provided with a memory,
control input means, and
display means.

According to one preferred embodiment of the invention, the memory contains:
a sequence to calibrate the signal transmitted by the transmission means as a function of the stride length and intrinsic parameters of the shoes,
a stride length estimating algorithm,
an algorithm to calibrate the signal transmitted by the transmission means as a function of the parameters input by a user, and
an algorithm to estimate the stride speed.

Preferably, the calibration sequence is designed firstly to determine a mathematical calibration law by means of a polynomial regression, and secondly to determine a direct correspondence between the measured signal and the stride length, for given shoes and a given individual.

Preferably, the stride length estimating algorithm uses the measurement of the variation in the magnetic field resulting from the movement of the magnetic mass.

BRIEF DESCRIPTION OF THE DRAWINGS

This invention will be better understood after reading the description of example embodiments given below, purely for guidance and in no way limitative, with reference to the attached drawings in which.

DETAILED DESCRIPTION OF THE PREFERRED EMBODIMENTS

Figure 1:
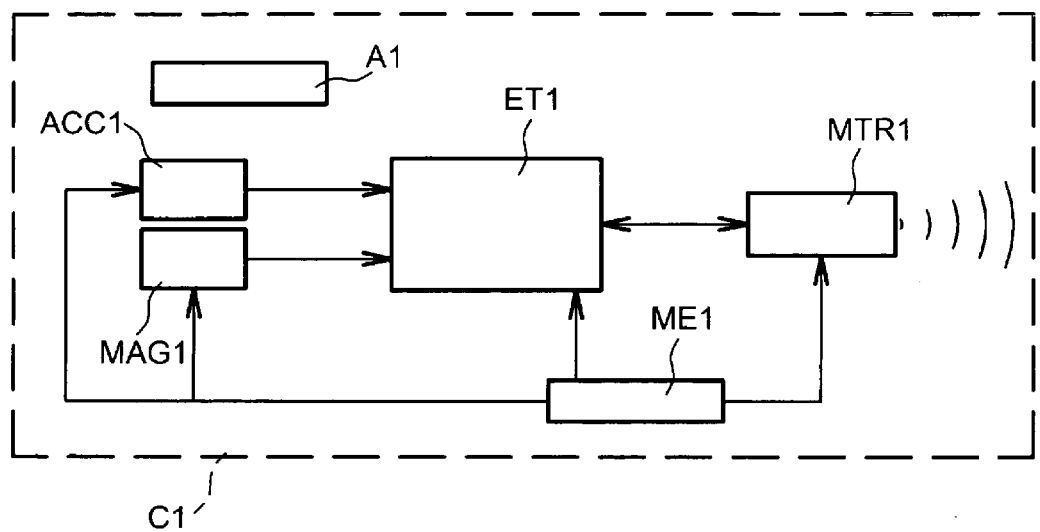
FIG. 1 is a diagrammatic view of part of a particular embodiment of the device according to the invention that is contained in one of the shoes in a pair of shoes.

The following describes examples of the device according to the invention, in which the fact that at all times in a stride, one foot has a support point fixed with respect to the ground while the other foot is moving, at a variable distance from the foot with a support point fixed with respect to the ground, and this distance is measured to calculate the distance travelled by integration.

These examples involve the combined association and processing of signals from one or several magnetometers (preferably one or several micro-magnetometers) and one or several accelerometers contained in one of the shoes in a pair of shoes, and a magnetic mass contained in the other shoe in the pair, to measure mainly distances and speeds.

Thus, at least one magnetometer is used, and preferably a micro-magnetometer to measure the magnetic field produced by a moving magnetic mass, to make a dynamic measurement of the distance between the shoes using the measurement of the response of the signal from the magnetometer. This measurement uses the signal shape and the amplitude of the alternating magnetic field that is measured at the rate of the stride.

This dynamic measurement is calibrated in time using the signal output by the accelerometer, particularly at the time of the impact of the foot on the ground and the calibration makes it possible to determine the instants at which the signal from the micro-magnetometer has to be processed.

This measurement can be corrected or refined by joint integration of the acceleration measured by the accelerometer, the measured speed of the mobile magnetic mass and then the measured distance between the shoes.

This measurement will be calibrated by a calibration phase to establish the law defining the stride length as a function of the signal amplitude and as a function of the walker or runner and magnetic characteristics of the shoe containing the magnetic mass.

In one variant of the device, a differential measurement can be made between the micro-magnetometer located in the shoe and another micro-magnetometer that is at a distance from this shoe and that may for example be located in a bracelet, to subtract the earth's magnetic field (measured by this other micro-magnetometer) from the magnetic field measured by the micro-magnetometer located in the shoe, so as to determine the signal/noise ratio and therefore the measurement precision.

In the given examples, the shoes are provided with completely standalone and portable means.

The measured parameters are preferably transmitted by radio to personal display and monitoring means that can be installed on a bracelet or on any other portable element.

A device conforming with the invention can be made in order to measure various parameters, and particularly the number of steps, the length of each step, the distance travelled, the walking or running time, the average speed of the walker or the runner, his maximum speed and his rest time.

This device can be programmed to define a typical hike, particularly by the duration, speed, rhythm and rest time, and to measure differences between effective values and planned values so that the user can perform a defined program.

This device may include two additional micro-magnetometers in order to save directions and/or the route and/or the heading followed by the user of the device.

All parameters are transmitted to portable display means (that can be fixed to a belt or a bracelet).

Furthermore, a device conforming with the invention may be used with a watch and/or an altimeter and/or a temperature measurement means and/or a micro-magnetometer (to measure the earth's magnetic field as mentioned above), and/or a means of measuring the heart rate at the wrist.

An energy index of the person wearing the device may also be calculated:

$IE(t)=K. (a.Dm+b.Dd+c.Dh)(t)$ where:

$IE(t)$: energy index during time t,
a, b, c: weighting coefficients, in particular taking account of the weight of the person wearing the device.

Dm: value calculated as a function of the distance travelled when going uphill, with correlation of information provided by the altimeter.

Dd: value calculated as a function of the distance travelled when going downhill, with correlation of information provided by the altimeter.

Dh: value calculated as a function of the distance travelled in a horizontal phase, with correlation of information provided by the altimeter.

K: global coefficient, taking account of the units, nature and the difficulty of the ground.

An index of the power output during time t can be defined by the following formula:

$IP(t)=IE(t)/t.$

For high level sports applications or medical applications, a high sensitivity device according to the invention can be made using several accelerometers, several micro magnetometers and processing algorithms designed to make precise calculations of foot movements in space and different foot orientations, within a determined time phase.

A device according to the invention is installed in a pair of shoes. One of the shoes may be simply provided with a magnetic mass consisting of a magnet, preferably a permanent magnet.

The other shoe can simply include at least one accelerometer, at least one magnetometer, electronic means for processing signals output by the latter and an electric energy source to supply power to the accelerometer, the magnetometer and the electronic processing means.

The device may also comprise display, monitoring and control means that can then be placed on a bracelet or a belt, although this is not indispensable.

However, the two shoes preferably contain the same equipment, for reasons of industrial manufacturing, manufactured quantities, symmetry and homogeneity.

Figure 2:
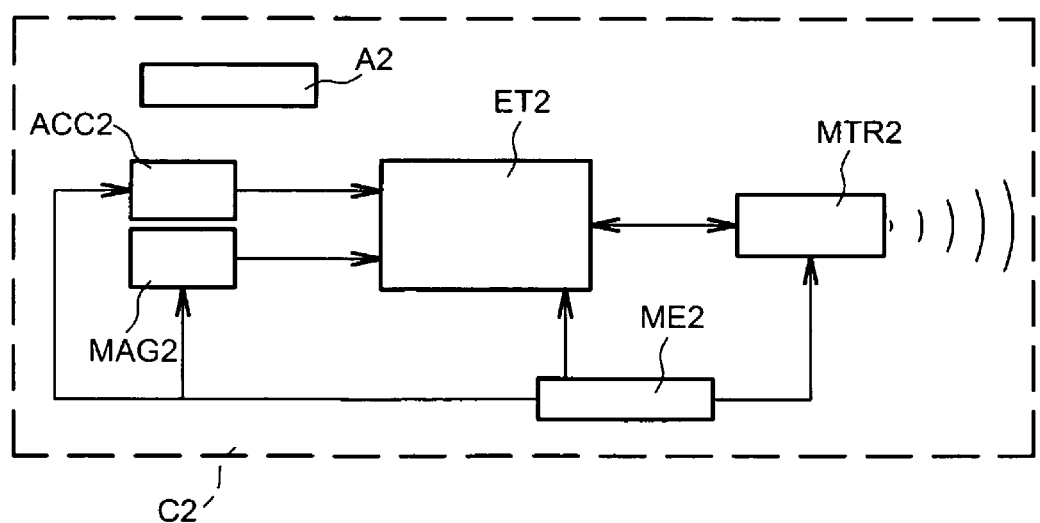
FIG. 2 is a diagrammatic view of another part of this device contained in the other shoe in the pair.

This is diagrammatically shown by the example in FIGS. 1 and 2 in which a device according to the invention is installed in a pair of shoes marked as references C1 and C2 in FIGS. 1 and 2, the shoe C1 for example corresponding to the right foot and shoe C2 to the left foot. It should be noted that these shoes are in the earth's magnetic field Bt.

For example, the various components of the device could be installed in the soles of shoes C1 and C2.

Shoe C1 (shoe C2) comprises:
- an accelerometer ACC1 (ACC2) or several accelerometers if necessary,
- a magnetometer MAG1 (MAG2) or several magnetometers if necessary,
- a permanent magnet A1 (A2) that generates a magnetic field B1 (B2),
- electronic processing means ET1 (ET2) to process signals output by the corresponding accelerometer and magnetometer,
- a transmission module MTR1 (MTR2) provided with an antenna (not shown) designed to transmit the signals thus processed, and
- an electric power supply module ME1 (ME2) designed to supply power to the corresponding accelerometer, magnetometer, electronic means and transmission module, and that may be a battery, an electromechanical generator or an accumulator rechargeable by remote power supply.

Figure 3:
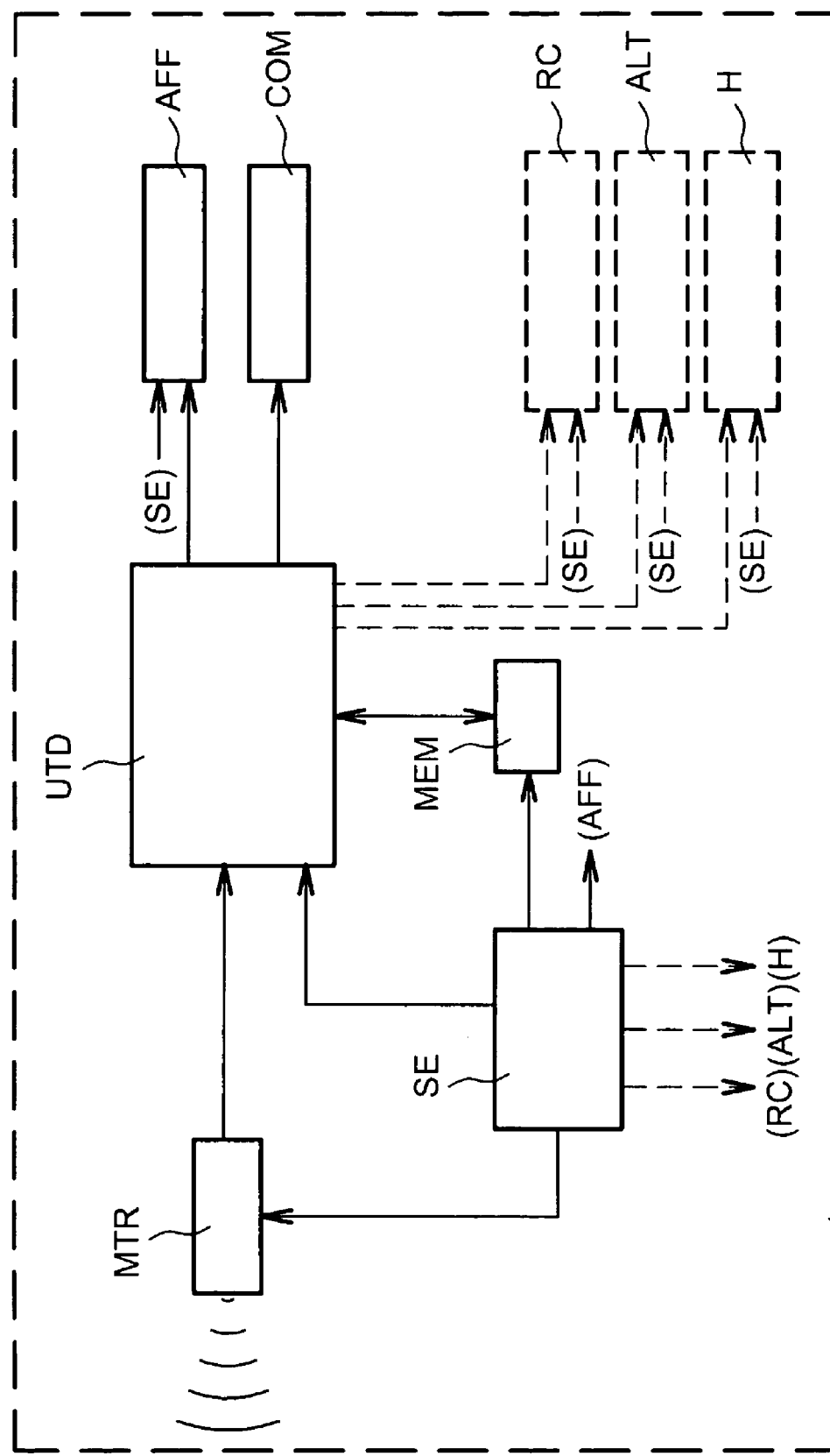
FIG. 3 is a diagrammatic view of monitoring and control means included in this device.

In the example considered, the person wearing the shoes thus equipped also has a monitoring and control bracelet (or belt) BCC as shown in FIG. 3, that comprises:

- a digital data transmission/reception module MTR, this module MTR being provided with an antenna (not shown) and being used for reception of data transmitted by the modules MTR1 and MTR2,
- a data processing unit UTD that is provided with a memory MEM, a control keyboard COM and means AFF for displaying data received through the module MTR, these data being displayed after they have been processed in the processing unit UTD, and
- an electric energy source SE, for example a battery, to supply energy to the module MTR, the unit UTD, the memory MEM, the display means AFF (and any other devices RC, ALT and H that may be included in the bracelet and that will be discussed later).

For example programs called SEQCAL, FOULEE, NORPARAM and ESTIVITS are saved in the memory MEM.

SEQCAL is a calibration sequence of the signal output by accelerometers and magnetometers, as a function of the stride length and intrinsic parameters of the shoe.

SEQCAL calculates the mathematical calibration law using a polynomial regression or any other appropriate algorithm, and sets up a direct correspondence between the measurement signal and the stride length for a given shoe and a given individual.

This correspondence depends on the internal magnetic mass, its distribution in the shoe (there is only one magnet per shoe in the example considered, but in another example there could be several), and the orientation of the magnetic dipole(s) of the magnetic mass.

FOULEE is an algorithm for estimating the stride length. This algorithm is based on processing of the signal generated by the variation of the magnetic field created by the "magnetic" shoe (it is called magnetic because it contains a magnet) when this shoe is moving.

The signal varies depending on the instantaneous distance between the micro-magnetometer and the shoe, the direction of magnetisation and the distribution of the magnetic mass in the shoe.

The UTD unit calculates the stride length as a function of the signal shape, its amplitude, the instant given by the accelerometer(s) for taking the magnetic signal of the stride into account, and the parameters in the law that are determined during the calibration phase.

The relations and algorithm given below are then used.

The magnetic signal B(t) measured at time t depends on a model that depends (as a first approximation) on the instantaneous distance (distance at time t) between the magnetic mass (magnet) of the shoe and the magnetometer(s) of the other shoe, according to the following relation:

$$B(t) = \frac{\mu 0}{4\pi}\left(\frac{3(M.r)r}{r^5} - \frac{M}{r^3}\right)$$

In this formula, the vectors are indicated by bold characters, $\mu o$ is the permeability of a vacuum ($4\pi \times 10^{-7}$ m.kg.c$^{-2}$), M is the magnetic moment of the magnet and r is equal to OP where O is the centre of the magnet and P is the measurement point.

The complete magnetic signature of the passage of one foot in front of the other depends on the minimum distance between the two feet and the speed V of the foot in the stride.

The minimum distance between the two feet is determined in the previous algorithm (SEQCAL). Therefore a correct estimate of the speed V can be obtained using a known quadratic differences minimisation process and an adapted filtering.

The impact times of the shoe are taken into account by threshholding of the accelerometer(s) during signal processing, and that makes it possible to determine the impact times t1 and t2 and to calculate the difference δt between them. The length L of the stride is then easily calculated and is equal to the product of the speed V (estimated) and δt.

It is possible that the magnetic signal is attenuated at the end of the stride and therefore that the measurement is too imprecise in this area (that represents a few % of the run or the walk).

Under these conditions, using the speed estimate made when the signal quality is good, it is easy to calculate the distance travelled in this area by multiplying the estimated speed by the path time corresponding to this area, for which the end is determined by when the accelerometer is tripped.

Furthermore, the quality of the measurement signal output by the micro-magnetometers contained in the shoes can be improved by correcting this measurement taking account of the value of the earth's magnetic field Bt. This is done by subtracting the measured value of Bt made by the micromagnetometer fixed to the bracelet or to the belt from this measurement, this magnetometer not being sensitive to the magnets in the shoes.

NORPARAM is an algorithm to calibrate signals as a function of parameters input by the user onto the keypad on the bracelet (or the belt).

ESTIVITS is an algorithm to estimate the stride speed. This algorithm takes account of the derivative of the signal output by the magnetometer in one shoe following a variation in the magnetic field generated by the magnet in the other shoe.

The bracelet (or belt) may also be provided with:
- a heart rate sensor RC composed of a pressure sensor to measure the pulse,
- a digital altimeter ALT for which the data as a function of time are saved in a memory that is initialised in each run (or each walk), and
- a clock H.

The unit UTD contains algorithms that are associated with these components RC, ALT and H and that are used to calculate secondary parameters.

In particular, an algorithm named INDEX is provided to calculate the energy index IE and the power index IP that were defined above, as a function of parameters a, b, c, and K.

Other algorithms may also be provided to calculate other parameters such as the distance travelled, the average speed, the maximum instantaneous speed, the total energy spent by the runner or the walker, the instantaneous energy integrated in different phases, the power output, the state of deviations from the run (or the walk) as a function of a previously defined program.

Furthermore, another algorithm called ORIENTATION may be provided to use signals from accelerometers, and particularly magnetometers that then should be bi-axial or tri-axial, to calculate the exact positions and orientations of the foot in space during the stride.

We will discuss such a processing at the end of this description.

If the magnetic mass that has to be placed in a shoe is too large, an electromagnet can be used to produce the magnetic field instead of a permanent magnet. Preferably, this electromagnet is placed in the sole of the shoe.

The energy to the electromagnet may be produced by a generator during each stride during the run or the walk, either at the time of the impact on the ground, or when the sole is folding. The battery is then used only to supply power to the remainder of the electronic means.

Figure 4:
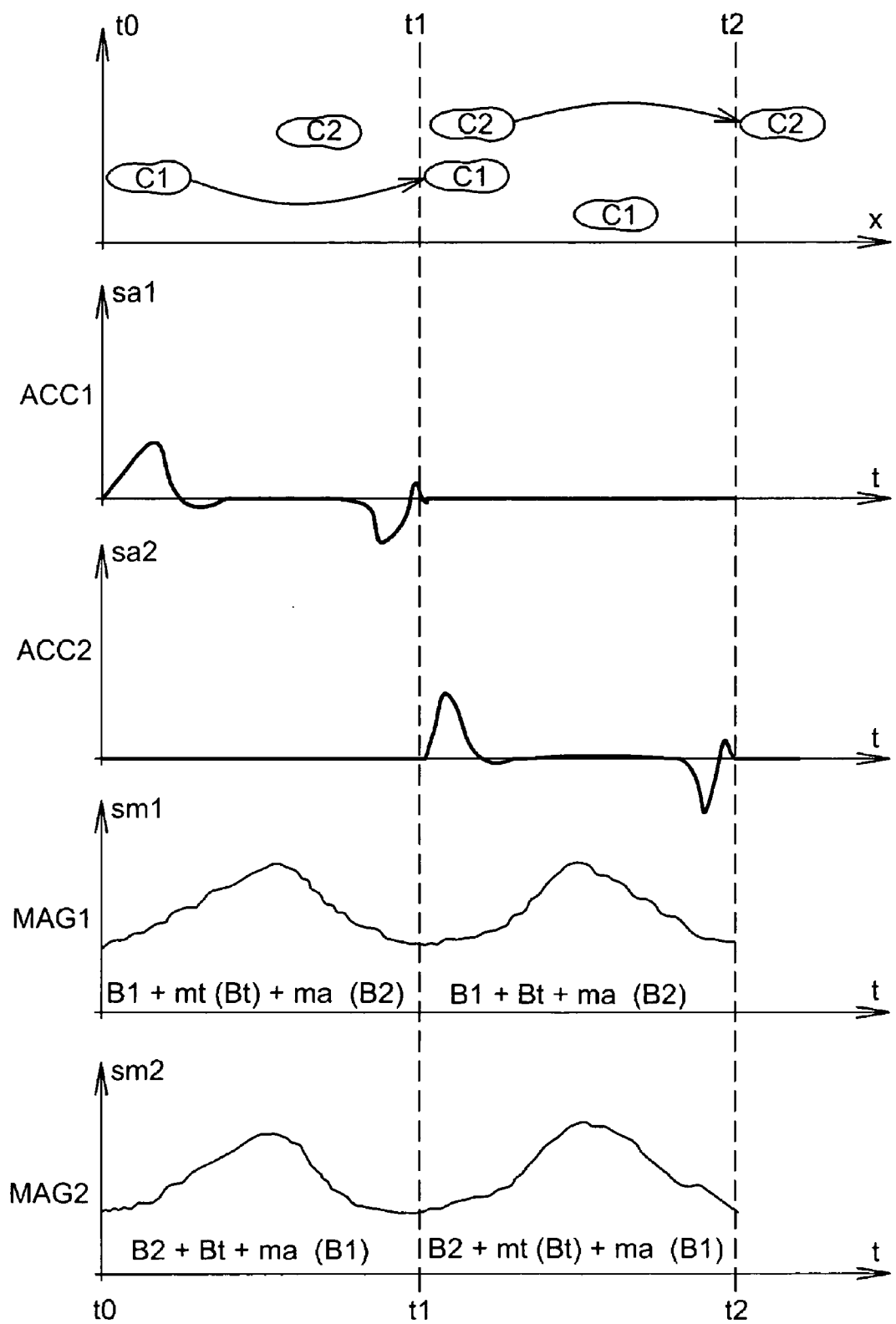
FIG. 4 is a diagram of signals received by components of this device, and FIG. 5 diagrammatically shows a movement pick up device.

FIG. 4 shows the diagram for signals sa1, sa2, sm1 and sm2 respectively received by accelerometers ACC1 and ACC2 and by magnetometers MAG1 and MAG2 as a function of time t.

The parameter x represents the distance travelled.

At time t0, the shoe C2 (left foot) is stopped and the shoe C1 (right foot) begins its stride movement that terminates at time t1.

Under these conditions, for signals received by C1:

ACC1 saves the acceleration then the deceleration of stride 1, and

MAG1 measures a signal s1 that is the sum of:
B1 that is a constant with time; it is known and can easily be subtracted;
mt(Bt) that is a modulation of the measurement of the earth's magnetic field during the stride, due to variations of the angle between MAG1 and vector Bt;
ma(B2) that is a modulation of the amplitude of field B2 during the stride, due to MAG1 passing close to magnet A2.

Concerning signals received by C2:

ACC2 does not measure any acceleration, since C2 is stopped, and the speed is zero;

MAG2 measures a signal s2 that is the sum of:
B2 that is a constant with time; it is known and can easily be subtracted;
Bt that is a constant for the entire stride;
ma(B1) that is a modulation of the amplitude of the field B1 during the stride.

At time t1 the stride 1 is terminated, C1 is stopped and C2 begins and then stops at time t2.

Operation is exactly the same but symmetric: signals with index 1 are replaced by signals with index 2 (and vice versa). Refer to FIG. 4.

We will now consider operation of the device.

The MAG1, ACC1, MAG2 and ACC2 signals are measured in analogue form and then converted into digital form by an appropriate converter.

These measurements are used in module ET1 (ET2) of shoe C1 (C2) using an interface (not shown) and are firstly stored in a memory with a FIFO (first in first out) type management, and secondly transmitted directly to the interface MTR1 (MTR2) that transmits them in encoded form, through a multi-channel digital radio transmission process.

For example, data for shoe 1 will be transmitted on MTR1 channel 1, and data for shoe 2 will be transmitted on MTR2 channel 2.

The sensors are sampled at a typical frequency of 100 Hz, that is adaptable.

In reception, the module MTR of the unit UTD of the portable monitoring—control means receives data streams and, depending on the reception channel, sorts these data in list mode in its memory, according to four different lists for MAG1, ACC1, MAG2 and ACC2.

A time indicator is inserted at the beginning of each list, so as to be able to mark each value of the corresponding encoders in time. The number of numeric values of sensors between two time indicators of the lists recorded in memory depends on the selected sampling frequency. For example, this number is equal to 100 if this frequency is equal to 100 Hz.

The storage capacity of unit UTD is such that at least all values of the sensors multiplied by the sampling frequency, multiplied by the maximum walking (or running) time to be recorded (for example 24 hours) can be stored.

The unit UTD continuously calculates parameters of the walk or the run, and to do so it triggers various calculation algorithms saved in its program memory.

The resulting data are displayed cyclically on the display means AFF, for example every 10 seconds, or when specifically requested by the walker or the runner.

The signals are recorded continuously over time and are stored in the memory.

The "FOULEE" and "ESTIVITS" algorithms are executed cyclically so as to calculate:
the stride speed and then the stride length, by integrating accelerometer signals, and
values of the stride speed and stride length by signal processing after subtraction of constant measurements of Bt, and stride modulation noise.

Acceptances of MAG1 and MAG2 signals are synchronised with starting of detection of the beginning of acceleration of ACC1 and ACC2 to take account only of "clean" signals, in other words with no disturbance.

Those skilled in the art could adapt the above examples to the case in which the shoe C1 is provided only with magnet A1, and shoe C2 is provided only with components ACC2, MAG2, ET2, MTR2 and ME2.

With this invention, a user can know the main parameters of his run or walk. Furthermore, the device according to the invention can easily be inserted in standard hiking or jogging shoes, due to its lightweight due to the use of integrated technologies enabling a reduction in weight and volume.

Figure 5:
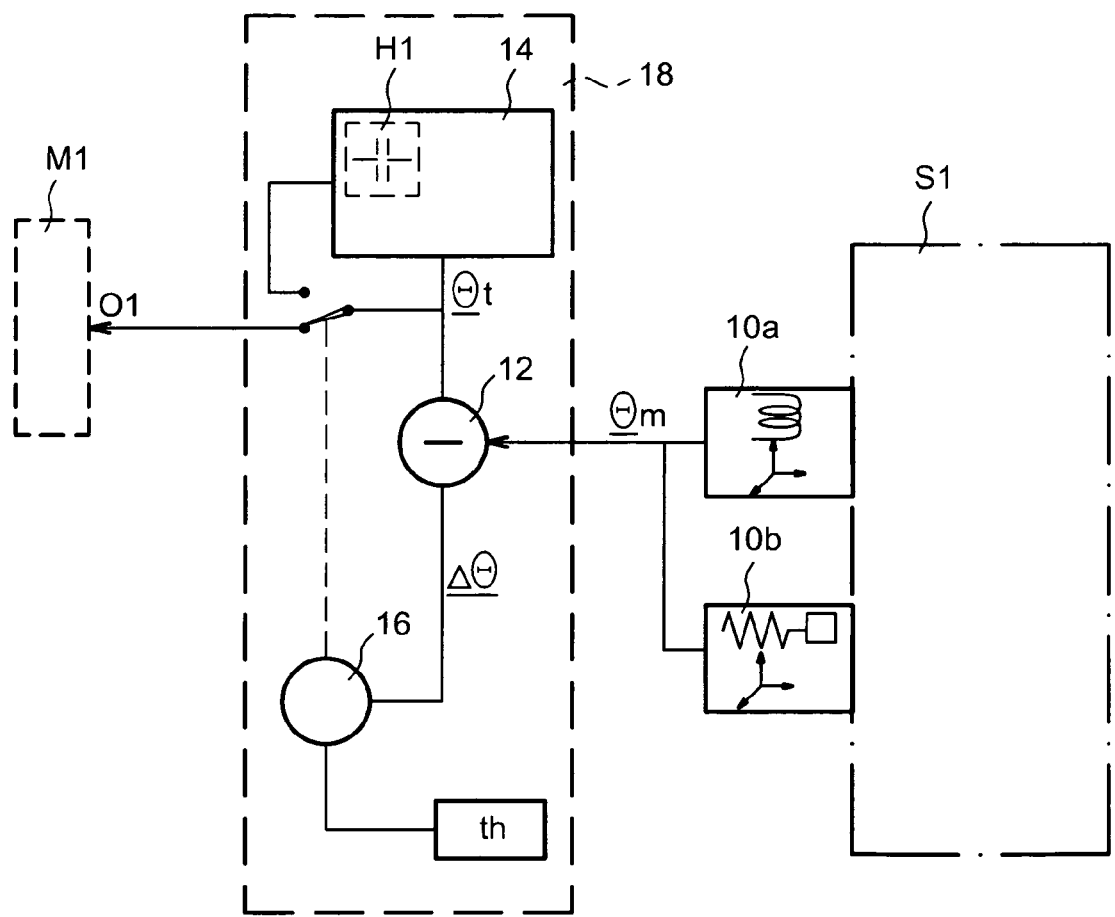

The following is an example of a technique used to create an algorithm to determine orientations of the foot in space, with reference to FIG. 5.

References 10a and 10b indicate an accelerometer and a magnetometer respectively. They are sensors with three sensitivity axes of a known type, capable of outputting measurement data representative of the orientation, in other words an angular position of a solid S1. The solid S1 is briefly indicated in discontinuous lines. For example, it could be part of the human body for which movements are to be estimated, a computer mouse, a surgical tool, etc.

Sensor measurements denoted $\Theta m$ are scalar or vector quantities. For example, they are representative of yaw, roll and pitch angles ($\phi$, $\psi$, $\theta$).

These measurements are directed towards a comparator 12. In the example shown, it is a differentiator. The comparator 12 also receives one or several test data $\Theta t$ output by a computer 14. The test data may be of the vector type and express angles along several axes. The computer 14 is used as a test data generation means. The test data are representative of an estimated orientation of the solid that may or may not be random. For example, they may be yaw, roll and pitch angle triplets ($\phi$, $\psi$, $\theta$). The computer may be located on the solid S1.

The comparator outputs a difference $\Delta\Theta$), which represents a deviation along one or several axes between the real orientation corresponding to the measurement data and the estimated orientation corresponding to the test data. This difference can be used to refine the estimated orientation of the sensor and therefore the solid to which it is fixed.

However, it is possible to fix a threshold th below which it is considered that the estimated orientation is sufficiently close to the measured orientation to be validated. This can take place using a second comparator 16 designed to compare the difference $\Delta\Theta$ with the threshold value th.

When the absolute value of the difference is less than the threshold, the test data $\Theta t$, in other words the estimate of the angular position is sent to an output O1.

However, when the difference is greater than the threshold, it is sent to the computer 14 to make a new position estimate.

The comparators 12 and 16 thus form means 18 of modifying the estimated orientation of the solid S1, with the computer 14.

The new estimate may be random. It may also be refined using a correction calculation using the error gradient reduction method.

The second comparator may possibly be eliminated. In this case, the estimated value is continuously refined until a new measurement value is input.

The device in FIG. 5 includes means, for example a memory, for saving successive, validated estimated values as a function of successive measurements of the angular position of the solid. The memory M1 may form part of the computer and it may be located on the solid S1. The successive values can be used to calculate the rotation movement, angular velocities and accelerations of the solid. The first generated test data to start the measurement of a new orientation of the solid is advantageously equal to the validated estimated value of the previous position.

A clock H1 can be used to clock the input of values of sensor measurements, and saving of estimated values in the memory M1.

An arbitrary number of sensors can be used, provided that this number is greater than the number of angle variables I to be estimated (the number of angle variables I to be estimated is between 1 and 3). Depending on the required quality of the estimate, it then becomes possible to use the minimum necessary number of sensors, or a number of sensors greater than the minimum number (redundancy).

The contribution of each sensor may be weighted. A confidence criterion or weight Cm is then set up and associated with each component of measurement Θm so that it can be used to some extent in the angle search algorithm. The calculation of a weight Cm is determined according to the following rules:
  a) the default value of the weight Cm is equal to 1,
  b) the value of the weight Cm is set to 0 in the case in which the output measurement is an aberrant value (saturation, value representing incorrect operation, etc.),
  c) the value of the weight Cm is equal to 0 when the noise level measured by the sensor is greater than a given threshold, an intermediate value varying linearly from 0 to 1 that can be applied for noise values varying from the threshold value to a noise value considered to be negligible,
  d) confidence is reduced on accelerometers if the total measured acceleration varies from the standard value of gravity,
  e) confidence is reduced on magnetometers if the magnetometers record an excessive variation from their standard (the presence of a ferromagnetic object(s) close to the sensor can then be suspected).

If there is no weighting, for an iteration made by the computer 14, the modification of a test angle I is related to the magnitude $S_I$ such that:

$$S_I = \sum_{n=1}^{N} (\alpha_{In} \Delta \Theta_n),$$

where
  n is the index of a sensor,
  N is the number of sensors,
  $\alpha_{In}$ is a parameter related to the sensor with index n, calculated in the normal manner by gradient reduction,
  $\Delta \Theta_n$ is the difference between the real orientation and the estimated orientation of the sensor with index n.

The introduction of a weight $Cm_n$ related to sensor with index n then modifies the expression of the magnitude $S_I$ as follows:

$$S_I = \sum_{n=1}^{N} Cm_n (\alpha_{In} \Delta \Theta_n)$$

In general, the values of a weight $Cm_n$ can vary continuously between the value 1 (total confidence on the measurement made by the sensor with index n), and the value 0 (total lack of confidence on the measurement made by the sensor with index n, the measurement made by the sensor with index n being ignored).

Thus, a method for estimating the orientation of a solid may include the following steps:
  a) input of measurement data from at least one angular position sensor and setting up test data representing an estimated orientation of the solid;
  b) comparison of the test data and the measured data,
  c) setting up a new test data representing a new estimated orientation of the solid, corrected as a function of the previous comparison,
  d) repetition of steps b) and c).

Steps b) and c) may be repeated until the comparison shows a difference less than a determined threshold between the test data and the measurement data.

A correction calculation can be made during the step c), using the so-called error gradient reduction method.

A comparison of test data and the measurement data may include setting up difference data, representing the difference between successive test data and the measurement data.

Steps a) to d) can be repeated with successive measurement data.

The invention claimed is:

1. A stride monitoring device, comprising:
  a first shoe including at least one magnetic mass;
  a second shoe including at least one magnetometer configured to measure a magnetic field produced by the magnetic mass in the first shoe and to output magnetic field signals based on the measured magnetic field produced by the magnetic mass in the first shoe, wherein said magnetic field signals can be processed to determine stride parameters and a distance between the shoes, and
  said second shoe further includes at least one accelerometer configured to measure an acceleration and to output acceleration signals based on the measured acceleration, and the accelerometer is further configured to output acceleration signals which are analyzed by a processor to determine instants of impact of said second shoe, and wherein the instants of impact are taken into account for calibrating in time a dynamic measurement of the distance between the shoes.

2. A device according to claim 1, wherein each of the first and second shoes includes the at least one magnetic mass, measurement means for making at least one physical measurement, and electronic means for processing the physical measurement, the measurement means including the at least one accelerometer and the at least one magnetometer configured to output signals that can be processed to determine the stride parameters.

3. A device according to claim 1, wherein the magnetic mass includes at least one permanent magnet.

4. A device according to claim 1, wherein the second shoe includes a plurality of accelerometers.

5. A device according to claim 1, wherein the second shoe includes a plurality of magnetometers.

6. A device according to claim 1, wherein the second shoe comprises said at least one accelerometer and electronic means for processing said magnetic field signals and said acceleration signals, wherein said electronic means comprises means for transmitting a signal output by the electronic means.

7. A device according to claim 6, further comprising portable means for receiving the signal transmitted by the means for transmitting and for displaying data representative of the signal.

8. A device according to claim 7, wherein the portable means comprises:
means for receiving data;
electronic data processing means for processing data, the electronic data processing means including a memory;
means for controlling inputs; and
means for displaying.

9. A device according to claim 8, wherein the memory includes:
a calibration unit configured to calibrate the signal transmitted by the transmission means, as a function of stride length and magnetic characteristics of the shoes,
a stride length estimating algorithm,
an algorithm to calibrate the signal transmitted by the transmission means as a function of the parameters input by a user, and
an algorithm to estimate the stride speed.

10. A device according to claim 9, wherein the calibration unit is configured to determine a mathematical calibration law by a polynomial regression, and to determine a direct correspondence between the measured signal and the stride length, for given shoes and a given individual.

11. A device according to claim 9, wherein the stride length estimating algorithm uses a measurement of a variation in magnetic field resulting from movement of the magnetic mass.

12. A device according to claim 1, wherein said second shoe includes said at least one accelerometer and electronic means for processing said magnetic field signals and said acceleration signals.

13. A device according to claim 1, further comprising electronic processing means for determining instants of impact of said second shoe based on said acceleration signals outputted by said accelerometer.

14. A device according to claim 13, further comprising calibration means for performing a calibration in time of the dynamic measurement of the distance between shoes based on the instants of impact.

15. A device according to claim 14, further comprising means for determining, based on said calibration, instants at which said magnetic field signals are to be processed.

16. A device according to claim 14, wherein said calibration means perform said calibration based on said acceleration signals output by said accelerometer.

17. A device according to claim 13, wherein said electronic processing means calculate a time difference between consecutive impact times and calculate a stride based on said time difference.

* * * * *